US006815174B1

(12) United States Patent
Poskus et al.

(10) Patent No.: US 6,815,174 B1
(45) Date of Patent: Nov. 9, 2004

(54) THIOREDOXIN-GLUTAMATE DECARBOXYLASE 65 FUSION PROTEIN

(76) Inventors: Edgardo Poskus, Beruti 110 5°A, Banfield (1828), Pcia. Bs. Aires (AR); Mario Roberto Ermacora, San Martin 2075, Banfield (1828), Pcia. Bs. Aires (AR); Mariana Lorena Papouchado, Maure 3151 4°C, Buenos Aires (1426) (AR); Silvina Noemi Valdez, Cervantes 1345, Buenos Aires (1407) (AR)

( * ) Notice: Subject to any disclaimer, the term of this patent is extended or adjusted under 35 U.S.C. 154(b) by 0 days.

(21) Appl. No.: 08/969,334

(22) Filed: Nov. 28, 1997

(30) Foreign Application Priority Data

Nov. 28, 1996 (AR) ....................................... P960105371

(51) Int. Cl.[7] ........................ C07K 14/00; G01N 33/53; G01N 33/564
(52) U.S. Cl. ........................ 435/7.4; 435/7.5; 435/7.95; 435/69.3; 435/69.7; 435/2.32; 436/506; 530/350
(58) Field of Search ........................ 530/350; 435/69.7, 435/7.3, 7.4, 7.5, 69.3, 2.32, 7.95; 436/506

(56) References Cited

U.S. PATENT DOCUMENTS

| | | | | |
|---|---|---|---|---|
| 5,270,181 A | * | 12/1993 | McCoy et al. | 435/69.7 |
| 5,529,752 A | * | 6/1996 | Pontis et al. | 422/63 |
| 5,547,847 A | * | 8/1996 | Hagopian et al. | 435/7.4 |
| 5,674,978 A | * | 10/1997 | Tobin et al. | 530/326 |
| 5,858,724 A | | 1/1999 | Novy, Jr. et al. | 435/69.6 |

OTHER PUBLICATIONS

Papouchado, M.L. et al. Expression of properly folded human glutamate decarboxylase 65 as a fusion protein in *Escherichia coli*. Eur. J. Biochem. 246:350–359, Jun. 1, 1997.*

Davis et al., Biotechnology and Bioengineering, vol. 65, No. 4, p. 382–388, (1999).

Davis et al., Biochemical and Biophysical Research Communications, vol. 267, No. 3, p. 777–782, (2000).

Kapust et al., Protein Science, vol. 8, p. 1668–1674, (1999).

Papouchado et al., Journal of Autoimmunity, vol. 9, p. 689–697, (1996).

Richter et al., Hybridoma, vol. 15, No. 2, p. 103–108, (1996).

Schwartz et al., J. Mol. Biology, vol. 287, p. 983–999, (1999).

Sun et al., Biochemistry and Molecular Biology International, vol. 46, No. 3, p. 479–486, (1998).

Tuomi et al., Clinical Immunology and Immunopathology, vol. 71, No. 1, p. 53–59, (1994).

Wang et al., Biochem. J., vol. 338, p. 77–81, (1999).

* cited by examiner

*Primary Examiner*—David Saunders
(74) *Attorney, Agent, or Firm*—Birch, Stewart, Kolasch & Birch, LLP

(57) ABSTRACT

The present invention relates to a novel protein, a recombinant fusion hybrid, thioredoxin-human glutamate decarboxylase 65 and to a method of using such fusion protein in assaying anti-human glutamate decarboxylase antibodies for the diagnosis of insulin dependant diabetes mellitus. The present invention is further related to methods isolating said fusion protein ans said biotinylated fusion protein. Methods of detecting anti-glutamate decarboxylase 65 antibodies in human serum using either an *E. coli* protein thioredoxin-glutamate decarboxylase fusion protein or *E. coli* protein thioredoxin-glutamate decarboxylase-biotin as an antigen are disclosed.

9 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 10 amino acids
      (B) TYPE: Amino acid
      (C) STRANDEDNESS: Not Applicable
      (D) TOPOLOGY: Linear (xi) SEQUENCE DESCRIPTION: SEQ ID NO:1:

Gly Ser Gly Ser Gly Asp Asp Asp Asp Lys
               5                    10

THIOREDOXIN-GLUTAMATE DECARBOXYLASE 65 FUSION PROTEIN

BACKGROUND OF THE INVENTION

The present invention refers to a novel hybrid recombinant protein formed by the fusion of the *E. coli* protein thioredoxin (Trx) and the human enzyme, glutamate decarboxylase 65 (GAD65). The chimera Trx-GAD65, which does not exist naturally, is immunologically adequate to replace human GAD65 for the determination of anti-GAD auto antibodies in human serum, with the advantage with respect to natural human GAD65 that it can be produced in *E. coli* cultures with good yield and at low cost. The present invention also includes a method for the production of said protein, alone or in a biotinylated form, as well as applications of said protein in the diagnosis of diabetes mellitus.

Diabetes Mellitus is a severe disease that results in serious consequences for both afflicted individuals as well as society at large. It has been calculated that 5% of the population is afflicted with some type of diabetes. One fifth of the afflicted individuals require, sooner or later, administration of insulin in order to survive. In Argentina, there are more than 300,000 so afflicted individuals. The decision to administer insulin is made by the attending physician as soon as the patient's symptoms indicate the disease is full effect and the patient's pancreatic cells, the insulin producing cells, have been destroyed. At this stage, there is very little that can be done to arrest the progress of the disease.

Fortunately, certain markers have been discovered which permit the early discovery of the probable course of the disease, in individuals predisposed to irreversible forms of the disease, with great anticipation. These genetic and humoral markers allow for the implementation of preventive therapies. Further, animal studies have shown that certain preventative therapies have delayed the onset of the disease for years. Thus far, antibodies against glutamate decarboxylase are among the most efficient markers for insulin dependant Diabetes Mellitus. It would be beneficial to have a specific as well as economic detector for said antibodies.

GAD65 is an enzyme that catalyzes the formation of γ-aminobutyric acid from glutamic acid. It is present in several tissues, including nervous and pancreatic tissues.

Techniques available for the extraction and purification of GAD65 from human tissues do not allow for the extraction of sufficient quantities on the enzyme. Further, such techniques require extraction from human cadavers thereby involving complex legal and technical issues. Natural recombinant enzymes obtained from cell free in vitro systems is adequate for analytical methods, however, said techniques provide low yields and are costly.

Natural recombinant enzyme produced in insect cell cultures result in high yields and are useful for analytical methods, however, the method is lengthy, involved and costly.

Previous attempts at producing, in *E. coli* cultures, natural recombinant GAD65, in either it's native state or in an immunologically competent form for the detection of anti-GAD65, proved unsuccessful. In all those attempts, the resultant GAD65 was irregularly folded, had negligible specific enzymic activity and was recognized by a minority of anti-GAD65 positive patient serums. Other methods involving hybrid systems formed by fusing proteins or peptides to GAD65 were similarly not satisfactory.

Production of recombinant GAD65 in *E. coli* cultures is clearly of benefit from an economic stand point. Accordingly, it would be highly desirable to resolve the problems associated with the production of GAD65 in *E. coli* cultures.

It is known in the art of production of recombinant proteins that the gene of interest may be ligated to a second gene which is expressed satisfactorily in *E. coli* in order to generate a fusion protein and from said fusion protein the desired protein can be obtained. In particular, pTrxFus has been used as an expression vector for the union of genes that code for mammalian growth factors and cytokines (see, "A thioredoxin gene fusion expression system that circumvents inclusion body formation in the *E. coli* cytoplasm", Biotechnology 11, 187 (1993)). Said publication makes reference to the use of the pTrxFus vector as a means of producing soluble form proteins in an *E. coli* expression system. Further, it also describes the importance of separating the polypeptide from thioredoxin to which it is untied so as result in a practical method for the production of pharmaceutical proteins. Normally, fusion protein is a form of production of the selected protein, that is then separated from the thioredoxin for later use. Separation from the thioredoxin is a necessary step so that it will not interfere with the physico-chemical, biological and immunological properties of the desired protein.

In addition, it is necessary to have an antigen for the detection of anti-GAD antibodies, that is available in quantity, has a high degree of purity, is low cost, and allows one to overcome the difficulties which exist presently in the quantitative assaying of anti-GAD antibodies.

Current techniques for the detection of anti-GAD are radiometric, extremely labor intensive and require highly sophisticated laboratories. Presently, there is no method in the market which is precise, accessible, inexpensive and whose performance characteristics allow for anti-GAD tests on mass scale and away from research laboratories. The present invention has solved one of the principal problems that prevented the development of economic and widely available anti-GAD method of detection: recombinant GAD65 has been produced, in soluble form which is both enzymically and immunologically active, in great quantities and at low cost, as a fusion protein with the thioredoxin peptide.

That the fusion product Trx-GAD65 be expressed correctly in *E. coli* and also conserve, unaltered, it's immunochemical properties was not obvious over the prior art. Particularly in light of prior attempts to express GAD65, alone or as a fusion protein (fused with other peptides other than thioredoxin but used in the art of expression of recombinant proteins).

In addition, the fact that it is not necessary to remove the thioredoxin peptide from the Trx-GAD65 fusion product in order to obtain an adequate antigen could not be anticipated by knowledge of the art.

ELISA assays are easy to perform and highly sensitive. Nevertheless, these type assays in the detection of anti-GAD antibodies present two problems: the first is that an antigen is necessary that is available in sufficient quantity, has a high degree of purity and is of low cost. Therefore, having recombinant protein produced in a prokaryotic system having full immunoreactivity with anti-GAD would satisfy all those requirements and would be ideal for the development and implementation of these assays. Another important problem with ELISA assays is that is many of these assays (particularly in those in which the antigen is adsorbed directly to the solid phase) the antigen loses, either partially or totally, it's native structure. Since serum anti-GAD is directed towards conformational epitopes, loss of native structure could result in loss of immunoreactivity. This would explain why all conventional ELISA for anti-GAD described in the literature to date show a sensitivity (determined in new patients with DMID) of 25 to 30%, which is well below the reference method. In order to resolve this difficulty, at least in theory, the ELISA assay conditions may be altered in order to preserve the structure and access of conformational epitopes of the protein. Among the conditions that may be varied are the ELISA capture methods in which the protein is indirectly joined to the solid phase as well as other alternatives where the antigen and serum are pre-incubated where the antigen-antibody reaction occurs in solution and is then detected via the non-reactive antigen by ELISA.

In, "DELISA: sensitive non-isotopic assay for GAD65 antibodies, a key risk-assessment marker for insulin-dependant diabetes mellitus," Clinical Chemistry 42:2 263–269 (1996), a method is described for the incubation of human serum containing anti-GAD antibodies with biotinated GAD65 (bGAD65) which is then treated with avidin. Avidin complexes with free bGAD65 but not with bGAD65 which has formed immunocomplexes. The bGAD65-avidin complex is then assayed with an anti-GAD antibody conjugated with peroxidase. This assays results in good sensitivity and specificity, however, it relies on GAD65 obtained from insect cultures which as mentioned above has shortcomings.

Presently the most widely used assay for anti-GAD antibodies is one involving the use of a radio ligand (RBA), in which 35S-Methionine-GAD65 produced from lysed reticulocytes is used. (See, Grubin, C. E. et al (1994) Diabetologia 37,344–350; Petersen, J. S. et al, (1995), Diabetes 43, 459–467.) This assay is specific and sensitive and requires small amounts of antigen, however, it has the disadvantage that it requires a highly sophisticated laboratory to conduct the assay.

SUMMARY OF THE INVENTION

The present invention presents a novel protein, a recombinant fusion hybrid, thioredoxin-human glutamate decarboxylase 65. Said protein is particularly useful in assaying anti-human glutamate decarboxylase antibodies for the diagnosis of insulin dependent diabetes mellitus (DMID). Said protein has a stable shelf life if stored under proper conditions. This novel protein is particularly suited for currently available assays used to determine anti-GAD antibodies, including assays involving the incorporation of biotin as well as new methods which will be described herein below and form part of the present invention. Moreover, the present invention is directed at a biotinylated form of the fusion protein.

The present invention is further directed at methods of isolating said fusion protein and said biotinylated fusion protein.

The present invention id further directed towards methods of detecting anti-GAD65 antibodies in human serum using either the Trx-GAD fusion protein or Trx-GAD-biotin as an antigen.

DESCRIPTION OF THE PREFERRED EMBODIMENTS

The present invention is directed towards a novel fusion protein—thioredoxin-human glutamate decarboxylase 65 (Trx-GAD65). The protein is enzymically and immunochemically active and is useful in the assaying of anti-Gad antibodies. It is particularly useful in assays for insulin dependant diabetes mellitus and for non-insulin dependant forms of diabetes as well. The protein in question contains an amino acid sequence, beginning at the N-terminus and moving to the C-terminus, corresponding to E. coli thioredoxin followed by a connector decapeptide having the sequence Gly-Ser-Gly-Ser-Gly-Asp-Asp-Asp-Asp-Lys, followed by the human glutamate decarboxylase without the initial Methionine.

Trx-GAD65 is novel in that it is not naturally occurring nor has it been previously reported. Assays in which the recombinant GAD protein is separated from the thioredoxin, in which up to 50% of the thioredoxin has been removed, results in an important loss of both enzymic and immunochemical function, thereby eliminating Trx-GAD65 as a source of GAD65. Additionally Trx-GAM65 allows for the design of novel assay techniques to determine levels of anti-GAD antibodies in human serum due to the combined immuno-properties of both Trx and GAD65.

Another important aspect to take into account is that the Trx portion allows for a one step purification of Trx-GAD65 utilizing affinity chromatography using an arsenic based derivative attached to a matrix thereby obtaining a specific activity of Trx-GAD65 of 2.0 U/mg. This specific activity appears to be the highest achieved thus far based on literature reports for GAD65 (See, Moody, A. J., et al (1995), Diabetologia 38, 14–23) with the following exceptions: A) natural human GAD65 purified from brain tissue has been reported at 51 U/mg (See, De Aizpurua, H. J., et al (1992) Proc. Natl. Acad. Sci. USA 89, 9841–9845), this value being out of line with other values reported, and is therefore believed to be an overestimation; b) GAD65 preparation prepared by Mehta and others from vaculovirus have been reported in the rage of 6.7–8.2 U/mg (See, Mehta, H. B., et al (1996), Clin. Chem. 42, 263–269), although these values are not comparable to the values reported in the instant invention since these were assayed utilizing different assay methods.

The present invention is further directed to the novel protein Trx-GAD65 in biotinylated form, that contains on average approximately 20 molecules of biotin per molecule of protein. Trx-GAD65-biotin allows for the design of novel methods to assay anti-GAD in human serum. Trx-GAD65 of the present invention has at least two novel properties. First, it allows for the elimination of natural GAD65 produced in eukaryotic cells as the control molecule in anti-GAD antibody from human serum assays. This is based on the belief that Trx-GAD65 has all the properties of GAD65 in it's native form along with other properties resulting from the fusion with Trx, which allows for it's use in any application where native GAD65 may be used in which Trx does not interfere. Second, unlike GAD65, it is possible to produce Trx-GAD65 in E coli utilizing methodologies described herein and which further constitute the present invention.

The present invention is further directed to a method for the purification of Trx-GAD65 protein involving the steps of: a) joining the genes coding for thioredoxin and human GAD65 with a linker DNA fragment coding for the spacer peptide: Gly-Ser-Gly-Ser-Gly-Asp-Asp-Asp-Asp-Lys in which the thioredoxin appears at the N-terminus of the fusion protein, b) inserting said hybrid DNA sequence, using an adequate promoter, in a plasmid that may be used for protein; expression in E. coli; c) transforming said vector in a stock of E. coli bacteria; d) growing the transformed bacteria in and appropriate induction medium; e) induce protein expression; f) isolation and purification of said protein; and g) storing said purified protein at −20° C. in ph 7.0 25 mM Tris-HCl, 50 mM NaCl, 40% glycerol, 0.2 mM pyridoxal phosphate, 0.05% Tween 20 and 0.1% aprotinin.

The GAD65 gene has been cloned and sequenced in various laboratories and the results published as follows: Erlander, M. G., et al (1991) Neuron 7, 91–100; Suzuki, R., et al (1995) Gene 152, 257–260; Lee, D. S., et al Biochim. Biophys. Acta 1216, 157–160; Faulkner-Jones, B. E., et al (1993) Endocrinology 133, 2962–2972; Karlsen, A. E., et al (1991) Proc. Natl. Acad. Sci USA 88, 8337–8341; Mauch, L., et al (1993) Eur. J. Biochem. 212, 597–603.

The tertiary structure of GAD65 is unknown, nor is the location of disulfide links, if any, known. It is known that GAD65 contains a pyridoxal phosphate co-factor.

Thioredoxin from E. coli is one of the most well known proteins since it has been used as a model for structural studies as well as the study of protein folding. The thioredoxin gene has been cloned and sequenced. (See, Wallace, B. J., et al (1986), Thioredoxin and Glutaredoxin Systems, Holgrem, A. (Ed.); Hoeoeg, J.-O., et al (1984) Biosci. Rep. 4, 917–923; and Russel M. and Model, P. (1988) Biol. Chem. 263, 9015–9019.).

The linkage peptide is a decapeptide, Gly-Ser-Gly-Ser-Gly-Asp-Asp-Asp-Asp-Lys and is codified in the pTrxFus plasmid, (LaVaille, E R., et al (1993) Biotechnology 11, 187–193), and it's solo known function is to serve as a spacer with a recognition site for enterokinase.

Utilizing standard genetic engineering techniques, a hybrid gene was constructed that codes for thioredoxin from E. coli, human GAD65 and the decapeptide linkage peptide. This chimeric protein consists, beginning at the N-terminus, of the thioredoxin sequence followed by the decapdptide linkage peptide followed by the GAD65 sequence minus the initial methionine residue.

The construction was realized by inserting the GAD65 gene (Karlsen, A. E. et al (1991) Proc. Natl. Acad. Sci. USA 88, 8337–8341) in the pTrxFus plasmid (LaVaille, E. R., et al (1993) Biotechnology 11, 187–193). This plasmid is commercially available (Invitrogen, San Diego, Calif.). In this plasmid, the thioredoxin-GAD conjugate is under the control of the PL promoter of λ bacteriophage that is inducible by tryptophan. Once the genetic construction is achieved it is incorporated into a GI 724 or GI 698 E. coli culture stock and protein expression was achieved via addition of tryptophan to these bacterial cultures.

Other vectors for expression of the Trx-GAD65 fusion protein are possible, so long as they contain and inducible promoter in a functional position. Additionally, other E. coli stocks would be useful so long as they are compatible with the selected expression vector.

The fusion protein was extracted from the bacteria through bacterial lysis and centrifugation. The protein is then further purified by use of affinity chromatography using an arsenic derivatized matrix (ThioBond, Invitrogen, San Diego, Calif.). The Trx-GAD65 thus purified is adequate for immunochernical assay use. An increase in the specific enzymic activity is obtained by use of a further purification step involving a molecular exclusion chromatography step. This step yields a GAD65 dimer with very low levels of contaminants. A further step involving molecular exclusion chromatography result in purification to homogeneity. The purified protein rapidly loses activity if stored in salt solution at low temperature. Accordingly, new storage methodologies have been developed utilizing solvents that preserve the protein's structure and activity.

Purification of the GAD65 moiety did not result efficient starting from Trx-GAD65. Treatment of the fusion protein with enterokinase for 24 hours, resulted in a loss of 50% of Trx, resulting in an important loss of the specific activity of GAD65 as a result of the long incubation period required for removal of the Trx polypeptide, thereby proving that obtaining native GAD65 from Trx-GAD65 is not feasible. Trx-GAD is a stable protein and Trx does not affect the tertiary structure and does not affect GAD activity.

In accordance with statements herein, the novel protein, Trx-human GAD is particularly useful in determine anti-GAD antibodies in human serum and may be used in current assays as well as novel assay techniques disclosed herein.

The present invention is further directed to a method for assaying anti-GAD antibodies for diagnosis of diabetes mellitus comprising the steps of:
 a) incubating human serum with the fusion protein Trx-GAD;
 b) adding the resultant mixture from step a to Protein A Sepharose FF (SIGMA, St. Louis, Mo.), centrifugation and subsequent collection of the supernatant;
 c) incubating said supernatant with polystyrene micro-platelets containing anti-GAD monoclonal antibodies and which have had non-specific binding sites blocked with fat-free powdered milk platelets;
 d) washing said micro-platelets with a PBS (0.14 M NaCl, 2.7 mM Kcl, 1.5 mM $KPO_4H_2$, 8.1 mM $Na_2PO_4H$, pH 7.4)-0.05% Tween 20;
 e) incubating said washed micro platelets with anti-Trx antibodies with rabbit biotin,
 f) washing said incubated micro platelets with PBS-Tween 20;
 g) incubating said washed incubated micro platelets with avidin conjugated with horse radish peroxidase (HRP);
 h) washing said incubated micro platelets with PBS-Tween; and
 i) assaying said peroxidase activity.

The present invention is further directed to a yet another method for assaying anti-GAD antibodies for diagnosis of diabetes mellitus comprising the steps of:
 a) incubating human serum with the fusion protein Trx-GAD;
 b) adding the resultant mixture from step a to Protein A Sepharose FF (SIGMA, St. Louis, Mo.), centrifugation and subsequent collection of the supernatant;
 c) incubating said supernatant with polystyrene micro platelets containing anti-Trx monoclonal antibodies and which have had non-specific binding sites blocked with fat-free powdered milk platelets;
 d) incubating said washed incubated micro platelets with avidin conjugated HRP;
 e) washing said incubated micro platelets with PBS-Tween; and
 f) assaying said peroxidase activity.

Rabbit serum containing anti-Trx was obtained by immunizing rabbits with Trx isolated, from GI 724 bacterias transformed with the pTrx vector (Invitrogen, San Diego, Calif.). Two antigen inoculations were done, spaced by a month. The first inoculation consisted of five subcutaneous injections consisting of 0.2 mg of Trx in complete Freund adjuvant, (Sigma, St. Louis, Mo.) each. The second inoculation consisted of the same protocol except incomplete Freund's adjuvant was used. Serum was collected from bleedings conducted 15 days after the second inoculation. Subsequently, the specific anti-Trx antibodies were purified by affinity chromatography. In order to a accomplish this, Trx was attached to Sepharose CL 4b activated with cyanogen bromide {Pharmacia-LKB Biotechnology, Inc., Uppsala, Sweden) following the standard protocol suggested by the resin manufacturer. The resin was then incubated overnight with immune rabbit serum at 4° C. with shaking, and then washed with 10 volumes of PBS and then eluted with 0.53% diethylamine (Sigma, St. Louis, Mo.) in $H_2O$ pH 11. The sample was collected in Tris-Hcl pH 8 and was the dialyzed overnight in PBS resulting in a final volume equivalent to the initial. The protein concentration of purified antibodies was 0.2 mg/ml as determined using Bradford's method.

The immonoreactivity of the serum, before and after purification was studied using an ELISA assay employing polystyrene platelets with Trx adsorbed (1 ug/well). The platelets were then blocked with fat-free powdered milk in 2% PBS and incubated with for 2 hours with 50% serial dilutions of the serum (final volume of 50 ul/well in Pbs-Tween). The wells were assayed using anti rabbit-HRP antibodies and o-fenilin diamide (OPD). The resultant color change was monitored at 495 nm OD. In both cases, serum before and after purification, titers of greater than 1/25600 were obtained.

Rabbit anti-Trx antibodies purified via affinity chromatography were biotinylated using sulfo-NHS-biotin. To accomplish this, the protein (0.2 mg at a concentration of 0.2 mg/ml) was incubated with 0.4 mg of biotin in a final volume of 1 ml of PBS, for 2 hours at room temperature. The mixture was then applied to a PD10 column (Pharmacia, Uppsala, Sweden) that had been previously equilibrated with PBS in order to remove unbound biotin. The titer of the biotinylated antibodies, which are to be used in ELISAs, was determined using platelets adsorbed to Trx and assayed with avidin-HRP (Sigma, St. Louis, Mo.), and found to be 1/200.

EXAMPLES

Example 1

Production of Trx-human GAD

Manipulation of Genetic Material

The sequence that codifies for GAD65 was ligated in the pTrxFus vector (Invitrogen, San Diego, Calif.). The resultant DNA codifies a Trx-GAD fusion protein comprised of bacterial thioredoxin followed by the decapeptide (Gly-Ser)$_2$Gly(Asp)$_4$Lys and human GAD65.

Expression of Trx-GAD65

The pGAD65(Trx) vector was transformed in GI 698 *E coli* bacteria using conventional methods of molecular biology. Expression of the cloned proteins in the pTrxFus vector was directedby the $P_L$ promoter that is regulated by the cl repressor of lambda bacteriophage that is expressed under control of the trp promoter.

PGAD(Trx) transformed GI 698 *E. coli* bacteria were grown at 30° C. in an induction medium (M9 slats, 0.2% cas amino acids, 0.5% glucose, 1 mM MgCl$_2$ and 100 ug/ml ampycilin) until OD$_{600}$=0.5. Protein expression was induced at 20° C. with 100 ug/ml tryptophan (Sigma, St, Louis, Mo.).

Isolation of Intracellular Soluble Fraction

After 12 hours of induction with tryptophan, the bacteria were collected via 7 min centrifugation at 5000 g. They were re-suspended in 1 ml lysis buffer (50 mM Tris-Hcl pH 7.0, 100 mM NaCl, 1 mM EDTA) per 50 mls of original cultivation medium. They were then lyzed by sonication employing four 20 sec pulses (Branson 450 Sonicator) in the presence of 1 mM 2-mercaptoethanol and protease inhibitors (0.1% aprotinin and 2 mM PMSF). After the sonication, Triton X-100 was added to a final concentration of 0.1% and the mixture was incubated for 10 min at 0° C. The soluble intracellular fraction was separated using 15 min centrifugation at 12,000 g.

The Trx-GAD fusion protein was purified using a affinity chromatography followed by molecular exclusion chromatography. For affinity chromatography ThioBond resin (Invitrogen, San Diego, Calif.) was used. This resin is an agarose resin containing attached Trx high affinity groups. In the purification, a volume of the bacterial soluble intracellular fraction was incubated for 1 hour at 4° C. in a half volume of ThioBond resin equilibrated in lysis buffer (50 mM Tris-Hcl pH 7.0, 100 mM NaCl, 1 mM EDTA, 1 mM 2-mercaptoethanol). The resin was then placed in a column and was washed in sequential form with 6 volumes of lysis buffer containing 1 mM 2-mercaptoethanol and 3 volumes of lysis buffer containing 5 mM 2-mercaptoethanol. Elution of Trx-GAD was realized using 2 volumes of lysis buffer containing 100 mM 2-mercaptoethanol.

The last step in the purification is realized through molecular exclusion chromatography using FPLC with a Superose 12 column (Pharmacia, Uppsala, Sweden). The column was calibrated with proteins of differing molecular weights (BioRad, Hercules, Calif.).

The fraction with a hydrodynamic volume equivalent to a Trx-GAD dimer corresponded to a Trx-GAD in greater than 90% purity and has a specific activity of 2.6 U/mg. This specific activity is comparable to that obtained for natural GAD65 (Moody, A. J., et al (1995) Diabetologia 38, 14–23).

Storage of Trx-GAD

Purified Trx-GAD was stored at −20° C. in 25 mM Tris-Hcl, 50 mM NaCl, 0.5 mM EDTA, 40% glycerol, 0.2 mM pyridoxal phosphate; 0.05% Tween 20 and 0.1% aprotinin. Storage under these condition allows for a shelf life of months. Whereas, storage under other conditions results in rapid loss of enzymic and immunochemical activity.

Example 2

Proteolysis of Trx-GAD using Enterokinase

Thioredoxin was removed from the fusion protein (purified using affinity chromatography as described in example 1) by means of digestion with enterokinase. Protein aliquots, 5 and 10 ug in 30 ul of 50 mM Tris-Hcl pH 8.1, 1 mM CaCl$_2$, 0.1% Tween 20 were incubated over night at 4° C. with 0.1 U EKMax (Invitrogen, San Diego, Calif.).

Results indicated that 50% of the thioredoxin had been removed with a resultant important loss of GAD65 specific activity as a result of the long incubation period required to remove said Trx, thereby demonstrating the difficulty in removing the Trx.

Example 3

Trx-GAD Enzymic Activity Determination

GAD specific activity was measured by means of measuring $^{14}CO_2$ formation from L-[U-$^{14}$C] glutamic acid. The assay was conducted in 15×100 mm glass tubes containing 2 ul of L-[U-$^{14}$C] glutamic acid (New England Nuclear, Boston, Mass.) with a specific activity of 251 mCi/mmol, 10 ul sample volume in a final volume of 200 ul of 50 mM potassium phosphate buffer pH 7.2, 1 mM EDTA, 1 mM 2-aminoethylisothioronium bromate, 0.2 mM pyridoxal phosphate, 20 mM glutamic acid. A small strip of 3MM Whatman paper imbued with 50 ul of 1 M hiamin in methanol (Sigma, St. Louis, Calif.) was folded and placed in each tube in a compact form. The tubes were then sealed with hermetic rubber caps. After the strips of paper expanded in each tube, the strip supported itself along the surface of the tube and in contact with the reaction mixture. After an incubation of 30 min at 37° C. in a shaking water bath, 0.2 ml of 2.5 M H$_2$SO$_4$ was injected through the rubber caps in order to stop the reaction. The reaction mixture was then further incubated for 60 min at 37° C. in order to assure the complete evolution of CO$_2$ and it's adsorption to the hiamiin. The strips of paper were then transferred to vials containing 3 mls of scintillation fluid (New England Nuclear, Boston, Mass.) and were allowed to sit overnight before being counted in the scintillation counter. GAD activity was expressed as units (U)/mg protein. One unit of GAD is equivalent to 1 umol of product formed per minute at 37° C. Protein concentration was determined using Bradford's method. (Read, S. M. and Northcote, D. H. (1981) Anal. Biochem. 116, 53–64) The most pure Trx-GAD preparations yielded specific activities of 2.6 U/mg.

Example 4

Immunoreactivity of Trx-GAD

Inhibition Studies

For this study the serum of 23 patients with DMID, in which anti-GAD had been detected by means of a reference radiometric assay (See, Grubin, C. E., et al (1994) Diabetologia 37, 344–350; Petersen, J. S., et al (1995) Diabetes 43, 459–467), were employed. These serums were retested for the presence of anti-GAD by means of immunoprecipitation with 35S-GAD65 marker (produced by lyzed reticulocytes) in the presence or absence of Trx-GAD (with a final concentration of 0.25 mg/ml). All serums that yielded positive results in the absence of Trx_GAD were negative in it's presence.

Displaceiment Curve

In order to establish the displacement curve the GAD65 positive by immunoprecipitation serum of a patient with DMID was selected. This serum contained, in significant quantities, only conformational anti-GAD antibodies since it failed to react in the same assay with denatured antigen. The serum was incubated with 35S-GAD65 marker (produced by lysed reticulocytes) in the presence of ten fold serial dilutions of Trx-GAD (concentrations ranging from 0.0003–30 $\mu$γ/ml). This assay resulted in the establishment of doses of Trx-GAD which causes 50% inhibition or displacement of the radioactive tracer which correspond to the same order of magnitude of the concentration of marker. Both concentrations were in the picomolar range. Therefore, GAD65 produced in reticulocytes is immunochemically very similar to Trx-GAD produced in bacteria.

Example 5

Preparation of Trx-GAD-biotin

Affinity purified Trx-GAD was biotinylated using sulfo-NHS-biotin (Pierce, Rockford, Ill.). To that end, 0.6 mg of Trx-GAD (0.5 mg/ml) was incubated with 0.08 mg biotin in a final volume of 1.2 ml for 2 hours at 0° C. The resultant mixture was applied to a PD10 column (Pharmacia, Uppsala, Sweden) that had been previously equilibrated with PBS in order to remove unincorporated biotin. Protein concentration for the biotinylated Trx-GAD was determined using Bradford's method. The number of biotin molecules incorporated per Trx-GAD molecule was determined by the HABA method (commercial system by Pierce, Rockford, Ill.), and yielded an incorporation of 20 molecules of biotin per molecule of Trx-GAD. The biotinylated protein was stored at −20° C. under the same conditions as described above for Trx-GAD.

Example 6

Process for the Determination of Human Anti-GAD Antibodies in Serum

Using Trx-GAD as the Antigen

Duplicate serums from DMID patients and controls were pre-incubated with Trx-GAD. 25 $\mu$l of each serum sample were incubated with 25 $\mu$l of PBS containing 0.1% BSA, 0.1% aprotinin, 0.05% Tween 20 and 80 pg of Trx-GAD for 18 hours at 4° C. As controls for maximal signal, two samples were incubated in parallel containing only Trx-GAD (no serum). 20 $\mu$l of Protein A Sepharose FF (with a final volume of 50 $\mu$l in PBS-Tween 20) were then added with shaking to each reaction sample during 2 hours. The samples were then centrifuged and the supernatants were transferred to ELISA plates prepared as follows:

a) incubation in 96 well polystyrene micro-plates of 0.5 $\mu$g/well of anti-GAD65 15 monoclonal antibody dissolved in PBS (50 $\mu$l/well) for 12 hours at 4° C.;

b) washing the micro-plates five times with PBS;

c) Blocking nonspecific binding sites with fat-free powdered milk in 2% PBS (300 $\mu$l/well) for a period of 2 hours at room temperature;

d) washing the micro-plates three times with PBS-Tween 20;

e) adding the supernatant from the pre-incubations (80 $\mu$l) and incubating for 2 hours at room temperature;

f) washing the micro-plates six times with PBS-Tween 20;

g) incubating said micro-plates with biotin conjugated anti-TRX polyclonal antibodies that are diluted 1/200 in powdered milk; and h) incubating said micro-plates with avidin-HRP.

B) Using Trx-GAD-Biotin as the Antigen

Duplicate serums from DMID patients and controls were pre-incubated with Trx-GAD-biotin. 25 ul of each serum sample were incubated with 25 ul of PBS containing 0.1% BSA, 0.1% aprotinin, 0.05% Tween 20 and 80 pg of Trx-GAD for 18 hours at 4° C. As controls for maximal signal, to samples were incubated in parallel containing only Trx-GAD-biotin (no serum). 20 ul of Protein A Sepharose FF (with a final volume of 50 ul in PBS-Tween 20) were then added with shaking to each reaction sample during 2 hours. The samples were then centrifuged and the supernatant were transferred to ELISA plates prepared as follows:

a) incubation in 96 well polystyrene micro-plates of 0.5 ug/well of anti-GAD65 monoclonal antibody dissolved in PBS (50 ul/well) for 12 hours at 4° C.;

b) washing the microplates five times with PBS; and c) incubating said micro-plates with avidin-HRP.

In all the described ELISAs the assays were developed by means of adding 50 $\mu$l O-phenylene-20 diamine, the HRP substrate (OPD, Pierce, Rockford, Ill.)., at a concentration of 1–2 g/l dissolved in 0.05 M citrate buffer pH 5 containing 0.06% $H_2O_2$ v/v (30 M). The reaction was stopped with 4 N $H_2SO_4$.

The calorimetric signal in each well resulting from the oxidized substrate was monitored by reading the optical density (OD) at 495 nm. In each ELISA, thespecific value of the OD for each serum was obtained by taking the control value (maximal signal) and subtracting the average of the two readings per sample serum.

Results 30 normal subjects and 42 patients with DMID were analyzed. The ELISAs employing either Trx-GAD or TRX-GAD-biotin yielded specificity of 97 and 93% using Trx-GAD and Trx-GAD-biotin respectively. It is worth mentioning that the control subject serums which gave positive results by ELISA were different than those which tested positive by the reference assay (RBA). The sensitivity of this assay was elevated: using Trx-GAD, 31 DMID patients were detected (74%), all of which tested positive by RBA, while using Trx-GDA-biotin resulted in 33 DMID patients testing positive (as was the case in the RBA test). That is to say that the ELISA using Trx-GAD-biotin resulted in the same sensitivity and specificity as the RBA assay. The Trx-GAD ELISA was somewhat less sensitive than RBA but showed greater specificity.

| Assay | Antigen used | Control (n = 30) (% positive) | DMID (n = 42) (% positive) |
|---|---|---|---|
| RBA | $^{35}$S-GAD | 93 | 78 |
| ELISAs | Trx-GAD | 97 | 74 |
|  | Trx-GAD-biotin | 93 | 78 |

The invention has been described in detail with particular reference to the above embodiments. It will be understood, however, that variations and modifications can be effected within the spirit and scope of the invention.

---

What is claimed is:

1. A thioredoxin-human glutamate decarboxylase 65 fusion protein comprising a recombinant hybrid biomolecule formed by the fusion of *E. coli* thioredoxin and human glutamate decarboxylase 65, having an amino acid sequence, beginning at the N-terminus, corresponding to *E. coli* thioredoxin sequence followed by a linkage decapeptide bearing the sequence $(Gly-Ser)_2Gly(Asp)_4Lys$ and followed by the human glutamate decarboxylase 65 sequence minus an initial methionine residue, wherein the fusion protein is in a soluble form wherein the glutamate decarboxylase 65 is both enzymatically and immunologically active.

2. The fusion protein according to claim 1, wherein said fusion protein is in a medium comprising 25 mM Tris-HCl, 50 mM NaCl, 0.5 mM EDTA, 40% glycerol, 0.2 mM pyridoxal phosphate, 0.05% Tween 20 and 0.1% aprotinin at −20° C.

3. A method of isolating and purifying a thioredoxin-human glutamate decarboxylase 65 fusion protein having an amino acid sequence, beginning at the N-terminus, corresponding to *E. coli* thioredoxin sequence followed by a linkage decapeptide bearing the sequence $(Gly-Ser)_2Gly(Asp)_4Lys$ and followed by the human glutamate decarboxylase 65 sequence minus an initial methionine residue wherein the fusion protein is in a soluble form wherein the glutamate decarboxylase 65 is both enzymatically and immunologically active and wherein said method comprises the steps of:

a) ligating a polynucleotide encoding said thioredoxin-human glutamate decarboxylase 65 fusion protein into a vector wherein said vector is suitable for expression in *E. coli* under the control of a suitable promoter in a suitable induction medium;

b) transforming said vector in a suitable strain of *E. coli* to generate a transformed *E. coli* strain;

c) growing said transformed *E. coli* strain in a suitable cultivation medium;

d) inducing protein expression; and e) isolating and purifying said thioredoxin-human glutamate decarboxylase 65 fusion protein.

4. The method of claim 3, wherein said suitable promoter comprises the $P_L$ promoter from λ bacteriophage.

5. The method of claim 4 wherein said suitable induction medium comprises MP salts, 0.2% cas amino acids, 0.5% glucose, 1 mM $MgCl_2$ and 100 μg/ml ampicillin.

6. The method of claim 5 wherein protein expression is induced by 100 μg/ml of tryptophan.

7. The method of claim 6 further comprising the step of storing said thioredoxin-human glutamate decarboxylase 65 fusion protein in a medium comprising 25 mM Tris-HCl, 50 mM NaCl, 0.5 mM EDTA, 40% glycerol, 0.2 mM pyridoxal phosphate, 0.05% Tween 20 and 0.1% aprotinin at −20° C.

8. A method for early detection of Diabetes Mellitus comprising detecting anti-human $GAD_{65}$ antibodies in human serum using a thioredoxin-human glutamate decarboxylase 65 fusion protein having an amino acid sequence, beginning at the N-terminus, corresponding to *E. coli* thioredoxin sequence followed by a linkage decapeptide bearing the sequence $(Gly-Ser)_2Gly(Asp)_4Lys$ and followed by the human glutamate decarboxylase 65 sequence minus an initial methionine residue wherein the fusion protein is in a soluble form wherein the glutamate decarboxylase 65 is both enzymatically and immunologically active and wherein said method comprises the steps of:

a) incubating human serum with said thioredoxin-human glutamate decarboxylase 65 fusion protein to generate an incubate;

b) adding said incubate to Protein A Sepharose FF, centrifuging to generate a pellet and a supernatant, with subsequent isolation of the supernatant;

c) incubating said supernatant in polystyrene micro plates containing adsorbed monoclonal anti-$GAD_{65}$ antibodies in which any nonspecific binding sites on the polystyrene micro plates have been blocked;

d) washing said incubated micro plates with a suitable first buffer to generate washed micro plates;

e) incubating said washed micro plates with rabbit anti-Trx biotin conjugated antibodies to generate second incubated micro plates;

f) washing said second incubated micro plates with a suitable second buffer to generate second-washed micro plates;

g) incubating said second-washed incubated micro plates with Horse Radish Peroxidase (HRP) conjugated avidin to generate third-incubated microplates;

h) washing said third-incubated micro plates with said suitable second buffer; and i) developing with HRP substrate to generate a measurable signal that provides an early detection of Diabetes Mellitus.

9. A method for early detection of Diabetes Mellitus comprising detecting anti-human $GAD_{65}$ antibodies in human serum using a biotinylated thioredoxin-human glutamate decarboxylase 65 fusion protein having an amino acid sequence, beginning at the N-terminus, corresponding to *E. coli* thioredoxin sequence followed by a linkage decapeptide bearing the sequence $(Gly-Ser)_2Gly(Asp)_4Lys$ and followed by the human glutamate decarboxylase 65 sequence minus an initial methionine residue wherein the fusion protein is in a soluble form wherein the glutamate decarboxylase 65 is both enzymatically and immunologically active and wherein said method comprises the steps of:

a) incubating human serum with said biotinylated thioredoxin-human glutamate decarboxylase 65 fusion protein to generate an incubate;

b) adding said incubate to Protein A Sepharose FF, centrifuging to generate a pellet and a supernatant, with subsequent isolation of the supernatant;

c) incubating said supernatant in polystyrene micro plates containing adsorbed monoclonal anti-Trx antibodies in which any nonspecific binding sites on the polystyrene micro plates have been blocked;

d) washing said polystyrene micro plates with a suitable buffer to generate washed micro plates;

e) incubating said washed micro plates with HRP conjugated avidin; and f) developing with HRP substrate to generate a measurable signal that provides an early detection of Diabetes Mellitus.

\* \* \* \* \*